United States Patent [19]
Pickart

[11] Patent Number: 5,023,237
[45] Date of Patent: Jun. 11, 1991

[54] METHODS AND COMPOSITIONS FOR HEALING ULCERS

[75] Inventor: Loren R. Pickart, Bellevue, Wash.

[73] Assignee: ProCyte Corporation, Redmond, Wash.

[21] Appl. No.: 401,312

[22] Filed: Aug. 30, 1989

[51] Int. Cl.$^5$ .................. A61K 37/02; A61K 37/14
[52] U.S. Cl. ................................. 514/18; 514/6; 530/330; 530/331
[58] Field of Search .............. 514/6, 18; 530/330, 530/331

[56] References Cited

U.S. PATENT DOCUMENTS

| | | | |
|---|---|---|---|
| 3,194,732 | 7/1965 | Neuhauser | 167/58 |
| 3,551,554 | 12/1970 | Herschler | 424/7 |
| 3,558,770 | 1/1971 | Gordon et al. | 424/80 |
| 3,758,682 | 9/1973 | Huber et al. | 424/177 |
| 3,767,784 | 10/1973 | Gluck | 424/28 |
| 3,832,338 | 8/1974 | Huber et al. | 260/113 |
| 4,022,888 | 5/1977 | Huber et al. | 424/177 |
| 4,167,945 | 9/1979 | Gottlieb | 128/334 R |
| 4,177,261 | 12/1979 | Dietze et al. | 424/101 |
| 4,263,428 | 4/1981 | Apple et al. | 536/17 A |
| 4,287,184 | 9/1981 | Young | 424/177 |
| 4,440,788 | 4/1984 | Terayama et al. | 424/320 |
| 4,665,054 | 5/1987 | Pickart | 514/18 |
| 4,760,051 | 7/1988 | Pickart | 514/18 |
| 4,810,693 | 3/1989 | Pickart | 514/18 |
| 4,877,770 | 10/1989 | Pickart | 514/18 |
| 4,937,230 | 6/1990 | Pickart | 514/18 |

FOREIGN PATENT DOCUMENTS 0078228 4/1982 European Pat. Off.
86/00222 1/1986 PCT Int'l Appl.

OTHER PUBLICATIONS

Pickart et al., "Growth-Modulating Tripeptide (glycylhistidyllysine): Association with Copper and Iron in Plasma and Stimulation of Adhesive and Growth of Hepatoma Cells in Culture by Tripeptide-Metal Ion Complexes," *J. Physiol.* 102(2):129-139, 1980.

Williams et al., "Glycyl-L-Histidyl-L-Lysine, a Growth Promoting Factor for Human Cells," *Cytobios* 27(105): 19-25, 1980.

Mochida Pharmaceutical Co., Ltd., "Anti-Inflammatory Injections Containing Superoxide Dismutase," Jpn. Kokai Tokkyo Koho, 81 07,720, Jan. 27, 1981 (cited in *Chem. Abstracts* 94:145386f, 1981).

Kwa, "Glycyl-L-Histidyl-L-Lysine: Synthesis of Analogs and NMR Studies," Ph.D. Thesis, University of Washington, 1983.

Loker, "Synthesis of Blood Serum Peptide Cell Growth Factors," Ph.D. Thesis, University of Washington, 1980.

Pickart, "The Biological Effects and Mechanism of Action of the Plasma Tripeptide Glycyl-L-Histidyl-L-Lysine," *Lymphonkines* 8:425-446, 1983.

Poole et al., "Stimulation of Rat Peritoneal Mast Cell Migration by Tumor-Derived Peptides," *Cancer Research* 43:5857-5861, 1983.

Raju et al., "Ceruloplasmin, Copper Ions, and Angiogenesis," *JNCI* 69(5):1183-1188, 1982.

Freedman et al., "Structure of the Glycyl-L-Histidyl-L-Lysine-Copper(II) Complex in Solution," *Biochemistry* 21:4540-4544, 1982.

Kwa et al., "PMR Studies of Cu(II) and Zn(II) Interaction with Glycyl-L-Histidyl-L-Lysine and Related Peptides," *Peptides: Structure and Function* 8:805-808, 1983.

(List continued on next page.)

*Primary Examiner*—Lester L. Lee
*Attorney, Agent, or Firm*—Seed and Berry

[57] ABSTRACT

A variety of compositions suitable for use with methods for (a) reducing the formation of stomach ulcers in warm-blooded animals, (b) reducing the secretion of stomach acid in warm-blooded animals, (c) increasing the secretion of cytoprotective mucous in the stomach of warm-blooded animals, and (d) healing established stomach or intestinal ulcers in warm-blooded animals are disclosed. The compositions include glycyl-L-histidyl-L-lysine, L-lysyl-L-histidyl-glycine, L-lysyl-L-histidyl-glycine:copper(II), glycyl-L-histidyl-L-lysine:copper(II), and derivatives thereof.

25 Claims, 4 Drawing Sheets

OTHER PUBLICATIONS

Perkins et al., "The Structure of a Copper Complex of the Growth Factor Glycyl-L-Histidyl-L-Lysine at 1.1 Å Resolution," *Inorganica Chimica Acta* 82:93-99, 1984.

Kimoto et al., "Enhancement of Antitumor Activity of Ascorbate Against Ehrlich Ascites Tumor Cells by the Copper: Glycylglycylhistidine Complex," *Cancer Research* 43:824-828, 1983.

Sorenson, "Copper Complexes: A Physiologic Approach to Treatment of Chronic Diseases," *Comprehensive Therapy* 11(4):49-64, 1985.

Pickart et al., "Inhibition of the Growth of Cultured Cells and an Implanted Fibrosarcoma by Aroylhydrazone Analogs of the Gly-His-Lys-Cu(II) Complex," *Biochem. Pharmacol.* 32(24):3868-3871, 1983.

Pickart et al., "Growth-Modulating Plasma Tripeptide May Function by Facilitating Copper Uptake into Cells," *Nature* 288:715-717, 1980.

"Newsreport on use of GGH-Cu(II) and Ascorbic Acid," *Natural Healing Annual* 1986, p. 38 (M. Bricklin (ed.), Prevention Magazine, Rodale Press, Emmaus, Pa.).

Pickart et al., "A Synthetic Tripeptide which Increases Survival of Normal Liver Cells, and Stimulates Growth in Hepatoma Cells," *Biochem. Biophys. Res. Commun.* 54(2):562-66, 1973.

Aonuma et al., "Studies on Anti-Ulcerogenic Protein in Inflamed Rabbit Skin Tissues," *Yakugaku Zasshi* 104(4):362-73, 1984.

Downey et al., "Acceleration of Wound Healing Using GHL-Cu(II)," *Surgical Forum* 36:573-75 (1985).

Pickart et al., "A Human Plasma Growth Factor with Superoxide Dismutase-like and Wound-healing Properties," Superoxide Dim. Chem., Biol. Med. Proc. Int. Conf. 4th 1985 (Pub. 1986), 555-57 (cited in *Chem. Abstracts* 106:13579c).

Frater-Schroeder et al., "Tumor Necrosis Factor Type α, a Potential Inhibitor of Endothelial Cell Growth in vitro is Angiogenic in vivo," *Proc. Natl. Acad. Sci. U.S.A.* 34:5277-81 (1987).

Pickart, "The Use of Glycylhistidyllysine in Culture Systems," *In Vitro* 17(6):459-66 (1981).

METHODS AND COMPOSITIONS FOR HEALING ULCERS

TECHNICAL FIELD

The present invention relates to the healing and/or prevention of ulcers in general, and more specifically, to the use of glycyl-L-histidyl-L-lysine, L-lysyl-L-histidyl-glycine, glycyl-L-histidyl-L-lysine:copper(II), L-lysyl-L-histidyl-glycine:copper(II), and derivatives thereof within a method for healing and/or prevention of ulcers in warm-blooded animals.

BACKGROUND OF THE INVENTION

The treatment of stomach ulcers remains a major health problem despite the development of numerous anti-ulcer medications. Traditionally, digestive ulcers have been treated through neutralization of excess stomach acid or through diet and behavioral or emotional modification. Well-known stomach acid neutralizers include sodium bicarbonate, magnesium hydroxide, calcium carbonate, aluminum hydroxide, aluminum phosphate, magnesium trisilicate, and tribasic calcium phosphate. Certain polyamine methylene resins have also been tried. Attempts have also been made to inhibit the flow of gastric acid, although these attempts are characterized by rather serious side effects. More specifically, while a compound referred to as cimetidine has been effective in stopping the secretion of stomach acid by blocking histamine sites, it has been found to have certain undesirable characteristics, including impairment of kidney function and mental confusion.

While certain low molecular weight compositions, such as salicylate-copper of diisopropylsalicylate-copper, have been reported to inhibit the production of stomach ulcers, these complexes tend to easily dissociate in the stomach into free copper and salicylate, which limits their practical use. In addition, these small copper complexes tend to be poorly soluble under aqueous conditions and must be administered with tissue-irritating solubilizing agents. Another such agent, the penicillamine-copper complex, often produces skin rashes and personality changes ("penicillamine psychosis").

More recent medical treatments involve the use of $H_2$ receptor blockers such as cimetidine, or the use of growth factors such as Epiderman Growth Factor (EGF, Urogastrone) or peptide fragments of EGF. However, these treatments suffer from a number of disadvantages, including instability, difficulty in synthesis and administration, and high production costs.

Therefore, there is a need in the art for an improved composition for healing and/or preventing the formation of ulcers. The present invention provides such composition, and further provides other related advantages.

DISCLOSURE OF THE INVENTION

Briefly stated, the present invention discloses a variety of pharmaceutical compositions suitable for use within the methods hereinafter described: (a) a method for reducing the formation of stomach ulcers in warm-blooded animals; (b) a method for reducing the secretion of stomach acid in warm-blooded animals; (c) a method for increasing the secretion of cytoprotective mucous in the stomach of warm-blooded animals; and (d) a method for healing established gastric (stomach) or duodenal (intestinal) ulcers in warm-blooded animals.

The compositions described herein include glycyl-L-histidyl-L-lysine (GHL), L-lysyl-L-histidyl-glycine (LHG), glycyl-L-histidyl-L-lysine:copper(II) (GHL-Cu), L-lysyl-L-histidyl-glycine:copper(II) (LHG-Cu), and various derivatives of GHL-Cu and LHG-Cu.

The derivatives of GHL-Cu have the general formula:

wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

In addition to the derivatives described above, other chemical modifications may be made to alter the biological activity of GHL and GHL-Cu derivatives. For instance, glycine may be replaced by a variety of other small amino acids, including alanine, serine, and valine. Further, the copper(II) binding affinity of the molecule may be increased by addition of an N-terminal amino acid, such as glycine, to convert glycyl-L-histidyl-L-lysine to glycyl-L-glycyl-L-histidyl-L-lysine. In addition, glycine could be added to a derivative as described above to create the corresponding tetrapeptide. The binding affinity for copper(II) of the imadazole group in the histidyl residue may be modified by substitution of 3-methylhistidine for histidine or by extending the lysyl side chains by adding additional carbon atoms to the chain.

The derivatives of LHG-Cu have the general formula:

wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

In addition to the derivatives described above, other chemical modifications may be made to alter the biological activity of LHG and LHG-Cu derivatives. For instance, lysine may be replaced by a variety of other small amino acids, including alanine, serine, and valine. Further, the copper(II) binding affinity of the molecule may be increased by addition of an N-terminal amino acid, such as glycine, to convert L-lysyl-L-histidyl-glycine to glycyl-L-lysyl-L-histidyl-glycine. In addition, glycine could be added to a derivative as described above to create the corresponding tetrapeptide. The binding affinity for copper(II) of the imadazole group in the histidyl residue may be modified by substitution of 3-methylhistidine for histidine or by extending the lysyl side chains by adding additional carbon atoms to the chain.

The methods described above generally comprise administering to the animal a therapeutically effective amount of one of the compositions described above in order to effect the desired purpose. Other aspects of the present invention will become evident upon reference to the following detailed description and attached drawing.

BEST MODE FOR CARRYING OUT THE INVENTION

As described herein, GHL, LHG, GHL-Cu, LHG-Cu and various derivatives thereof may be used in methods for (a) reducing the secretion of stomach acid in warm-blooded animals, (b) increasing the secretion of cytoprotective mucous in the stomach of warm-blooded animals, (c) reducing the formation of stomach ulcers in warm-blooded animals, and (d) healing established stomach or intestinal ulcers in warm-blooded animals. Derivatives of the present invention are described in detail in U.S. Pat. No. 4,665,054 and U.S. pat. application Ser. No. 312,295, now U.S. Pat. No. 4,877,770, which are hereby incorporated by reference. The derivatives of the present invention may be prepared by esterification, by the removal of a water molecule, or by the addition of a group (either an alcohol, such as octanol, methanol, benzyl alcohol, or $NH_3$) to the carboxylic acid terminus of GHL or LHG, resulting in the formation of a more lipophilic derivative.

GHL, LHG, GHL-Cu, LHG-Cu and several analogs have been tested in animal models of both gastric and duodenal ulcers. GHL-Cu, LHG-Cu and their analogs have been found to prevent gastric ulcer formation caused both by excessive acid secretion and by 95% ethanol ingestion. In the excessive acid (Shay) model system, increasing concentrations of GHL-Cu, LHG-Cu or analogs thereof decreased stomach acid secretion and resulted in fewer visible lesions when compared with saline controls. Pretreatment with GHL-Cu, LHG-Cu and analogs thereof was found to prevent gastric irritation and ulceration caused by ingestion of 95% ethanol. Administration of GHL-Cu, LHG-Cu and its analogs in the drinking water also accelerate the healing of ulcers caused by the ethanol.

GHL-Cu, LHG-Cu, and analogs thereof also accelerate the healing of established duodenal ulcers. In this model system, ulcers are induced by cysteamine injection. Briefly, rats with surgically confirmed ulcers were treated with GHL-Cu or LHG-Cu in the drinking water. At the end of the study, the treated rats exhibited both fewer ulcers and less severe ulcers than the control group.

GHL-Cu, LHG-Cu, and their analogs are also effective in preventing both gastric ulcer formation and in the healing of established gastric and duodenal ulcers.

The overall chemical reaction in the synthesis of GHL derivatives may be characterized:

$$GHL-OH + R-H \rightarrow GHL-R + H_2O.$$

In practice, the reaction is most readily carried out by adding the R group to the amino acid lysine prior to the combination of lysine with the other two amino acids to GHL. After the formation and isolation of GHL-R, the copper (II) is chelated to the molecule to form the bioactive complex.

The overall reaction to form the more lipophilic derivatives of GHL-Cu may be characterized:
(1) lysine-OH + R-H $\rightarrow$ lysine-R + $H_2O$
(2) lysine-R + blocked L-histidine $\rightarrow$ blocked L-histidine-L-lysine-R
(3) blocked L-histidine-L-lysine-R $\rightarrow$ partially blocked L-histidine-L-lysine-R
(4) partially blocked L-histidine-L-lysine-R + blocked-glycine $\rightarrow$ blocked glycyl-L-histidine-L-lysine-R
(5) blocked gycyl-L-histidine-L-lysine-R $\rightarrow$ glycyl-L-histidine-L-lysine-R
(6) glycyl-L-histidine-L-lysine-R + copper(II) $\rightarrow$ glycyl-L-histidine-L-lysine-R:copper(II).

The overall reaction to form the more lipophilic derivatives of LHG-Cu is the same as outlined above for GHL-Cu, except glycine-OH is the initial reaction component instead of lysine-OH, and blocked lysine is used in place of blocked glycine in step 4.

The results disclosed herein suggest that GHL, LHG, GHL-Cu, LHG-Cu, and derivatives thereof will exert healing actions on a variety of gastrointestinal diseases, such as colonic healing after anastomosis, lesions occurring subsequent to intestinal and bowel ischemia, necrotizing enterocolitis, and wounds of the mouth, throat, and esophagus. The general healing properties of GHL-Cu are described in U.S. Pat. Nos. 4,810,693 and 4,760,051, herein incorporated by reference.

Within a preferred embodiment, GHL or LHG, or a derivative of GHL-Cu or LHG-Cu are present in a 1:1 to 2:1 ratio. Within the present invention, it is generally preferred to administer the compositions described herein orally and in a capsule form. Methods for encapsulating compositions (such as in a coating of hard gelatin) for oral administration are well known in the art (Baker, Richard, *Controlled Release of Biologically Active Agents*, John Wiley and Sons, 1986). It is also generally preferred to administer the compositions in dosages from about 0.1 to 100 mg/kg of host body weight, although the dosage may be influenced by the condition of the patient. Further, it may be preferable to initially begin using a treatment of GHL-Cu or LHG-Cu, and then continue with treatment using the free peptide (GHL or LHG) with or without a small amount of copper(II).

To summarize the examples that follow, Example 1 illustrates the synthesis of glycyl-L-histidyl-L-lysine benzyl ester:copper(II). Example 2 demonstrates the synthesis of glycyl-L-histidyl-L-lysine n-octyl ester:copper(II). Example 3 illustrates (A) the synthesis of glycyl-L-histidyl-L-lysine n-stearyl ester:copper(II), and (B) its synthesis by an alternative procedure. Based upon either procedure, one skilled in the art could substitute n-palmityl alcohol (16 carbons) for the n-stearyl alcohol (18 carbons) to yield glycyl-L-histidyl-L-lysine n-stearyl ester:copper(II). Example 4 illustrates (A) the synthesis of glycyl-L-histidyl-L-lysyl-L-prolyl-L-valyl-L-phenylalanyl-L-valine:copper(II) and glycyl and glycyl-L-histidyl-L-lysyl-L-valyl-L-phenylalanyl-L-valine:copper(II) by solid-phase synthesis, and (B) the preparation of glycyl-L-histidyl-L-lysyl-L-valyl-L-phenylalanyl-L-valine by solution synthesis. Example 7 demonstrates the inhibition of stomach acid accumulation, the stimulation of cytoprotective mucous secretion, and a reduction in the formation of stomach ulcers in warmblooded animals. Example 8 demonstrates the healing of established stomach ulcers with GHL-Cu, LHG-Cu and derivatives thereof. Example 9 illustrates the healing of duodenal ulcers following oral administration with compounds of the present invention. Example 10 demonstrates the healing and prevention of ethanol-induced ulcers.

The following examples are offered by way of illustration and not by way of limitation.

EXAMPLES

Preparation of GHL, LHG, GHL-Cu and LHG-Cu for Use in Animals

GHL and LHG were purified by dissolving, in glass, distilled water (50 mg/ml), then centrifuging at 20,000 ×g for 1 hour at 3° C. This removes poorly water-soluble material remaining from the synthetic procedure. The supernatant is lyophilized, then passed through a Sephadex G-10 column at 3° C. in a solvent of 0.5% acetic acid. The main peak that elutes behind the solvent front (monitored by absorption at 254 nanometers) is lyophilized to dryness. GHL-Cu and LHG-Cu were prepared by combining purified GHL or LHG with equimolar amounts of cupric acetate and sodium hydroxide, then precipitated by use of ethanol addition and low temperature by published methods (Perkins et al., *Inorg. Chim. Acta* 67:93-99, 1984).

Sources of chemicals

Chemicals and peptide intermediates utilized in the following examples may be purchased from the following suppliers: Sigma Chemical Co. (St. Louis, Mo.); Peninsula Laboratories (San Carlos, Calif.); Aldridge Chemical Co. (Milwaukee, Wis.); Vega Biochemicals (Tucson, Ariz.); Pierce Chemical Co. (Rockford, Ill.); Research Biochemicals (Cleveland, Ohio); Van Waters and Rogers (South San Francisco, Calif.); Bachem, Inc. (Torrance, Calif.).

EXAMPLE 1

Synthesis of glycyl-L-histidyl-L-lysine benzyl ester:copper(II)

$N^e$-benzyloxycarbonyl-L-lysine benzyl ester was dissolved in 1:1 hexane-ethyl acetate and coupled to $N^a$-t-butyloxycarbonyl-$N^{im}$-benzyloxycarbonyl-L-histidine using dicyclohexylcarbodiimide as a coupling agent. Sodium bicarbonate (10%) was added and the product extracted into the organic layer. The product, $N^a$-t-butyloxycarbonyl-$N^{im}$-benzyloxycarbonyl-L-histidyl-$N^e$-benzyloxycarbonyl-L-lysine benzyl ester, was crystallized from solution. The N-terminal group of the blocked dipeptide was removed by stirring in 50% trifluoroacetic acid in dichloromethane for 30 minutes, then vacuum evaporated. The product, $N^{im}$-benzyloxycarbonyl-L-histidyl-$N^e$-benzoylcarbonyl-L-lysine benzyl ester, was coupled to lysine with dicyclohexylcarbodiimide as a coupling agent. Blocking groups were removed by catalytic hydrogenation using 10% palladium on carbon in glacial acetic acid. After lyophilization, the product, glycyl-L-histidyl-L-lysine benzyl ester, was dissolved in water and purified by ion-exchange chromatography on Dowex 50 X-4 cation-exchange resin and elution with 0.1M ammonium hydroxide, the eluate being immediately neutralized with acetic acid. A further passage through an anion-exchange column BioRex 63 at neutral pH removed breakdown products with free carboxylic acid groups.

The glycyl-L-histidyl-L-lysine benzyl ester was dissolved in water with equimolar copper acetate added. The pH was raised to neutrality with sodium hydroxide. The solution was centrifuged at 20,000×g for 1 hour at 3° C. to remove poorly water-soluble material. The supernatant was lyophilized to obtain glycyl-L-histidyl-L-lysine benzyl ester:copper(II).

EXAMPLE 2

Synthesis of glycyl-L-histidyl-L-lysine n-octyl ester:copper(II)

A mixture of $N^e$-benzyloxycarbonyl-L-lysine, n-octanol, benzene, and p-toluenesulfonic acid monohydrate was refluxed overnight using a DeanStark trap to remove water. After cooling, dry ethyl ether was added. The solution was then allowed to precipitate at 0° C. overnight. A portion of the precipitated solid was added to 50 ml potassium carbonate solution and 50 ml dichloromethane. After extraction, the layers were separated and the organic phase washed with water and brine, then dried with anyhdrous magnesium sulfate. Filtration, evaporation and purification by flash column chromatography gave n-octyl $N^e$-benzyloxycarbonyl-L-lysinate. The product was dissolved in tetrahydrofuran and mixed with $N^a$-t-butyloxycarbonyl-$N^{im}$-benzyloxycarbonyl-L-histidine, isobutyl chloroformate and N-methylmorpholine. After evaporation, water and ethyl acetate were added. The product was extracted into the organic phase, which was dried with anhydrous magnesium sulfate. Filtration, evaporation and purification by flash column chromatography gave n-octyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-octyl $N^{im}$-benzyloxycarbonyl-L-histidyl-$N^e$-benzyloxycarbonyl-L-lysinate. This was dissolved in tetrahydrofuran, and isobutyl chloroformate, N-methylmorpholine and benzyloxycarbonylglycine were added to form n-octyl benzyloxycarbonylglycine-$N^{im}$-benzyloxycarbonyl-L-histidyl-$N^e$-benzyloxycarbonyl-L-lysinate. This was dissolved in glacial acetic acid and hydrogenated overnight.

The resultant n-octyl ester of glycyl-L-histidyl-L-lysine was converted to the copper complex by the addition of an equimolar quantity of copper diacetate. The pH was raised to neutrality with sodium hydroxide. The solution was centrifuged at 20,000×g for 1 hour at 3° C. to remove poorly water-soluble material. The supernatant was lyophilized to obtain glycyl-L-histidyl-L-lysine n-octyl ester:copper(II).

EXAMPLE 3

A. Synthesis of glycyl-L-histidyl-L-lysine n-stearyl ester:copper(II)

A mixture of N$^e$-benzyloxycarbonyl-L-lysine, n-stearyl alcohol, benzene, and p-toluenesulfonic acid monohydrate was refluxed overnight using a Dean-Stark trap to remove water. After cooling, dry propyl ether was added to increase the total volume sixfold. The product was allowed to precipitate at 0° C. overnight and filtered. A portion of the filtrate was added to 50 ml potassium carbonate and 50 ml dichloromethane. After extraction, the layers were separated, and the organic phase was washed with water and brine, then dried with anhydrous magnesium sulfate. Filtration, evaporation and purification by flash column chromatography gave n-stearyl N$^e$-benzyloxycarbonyl-L-lysinate. The product was dissolved in tetrahydrofuran and mixed with N$^a$-t-butyloxycarbonyl-N$^{im}$-benzyloxycarbonyl-L-histidine and isobutyl chloroformate and N-methylmorpholine. After evaporation, water and propyl acetate were added and the product was extracted into the organic phase, then dried with anhydrous magnesium sulfate. Filtration, evaporation and purification by flash column chromatography gave n-stearyl N$^a$-t-butyloxycarbonyl-N$^{im}$-benzyloxycarbonyl-L-histidyl-N$^e$-benzyloxycarbonyl-L-lysinate.

The product was dissolved in 50% trifluoroacetic acid in dichloromethane for 30 minutes, then evaporated, forming n-stearyl N$^{im}$-benzyloxycarbonyl-L-histidyl-N$^e$-benzyloxycarbonyl-L-lysinate, which was dissolved in tetrahydrofuran, isobutyl chloroformate, N-methylmorpholine and benzyloxycarbonylglycine to form n-stearyl benzyloxy-carbonylglycyl-N$^{im}$-benzyloxycarbonly-L-histidyl-N$^e$-benxyloxycarbonyl-L-lysinate. The product was dissolved in 50% trifluoroacetic acid in dichloromethane for 30 minutes, then evaporated, forming n-stearyl ester glycyl-L-histidyl-L-lysine.

The resultant molecule, glycyl-L-histidyl-L-lysine n-stearyl ester, was converted to the copper complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

B. Alternative synthesis of glycyl-L-histidyl-L-lysine n-stearyl ester:copper(II)

N$^e$-benzyloxycarbonyl-L-lysine, n-stearyl alcohol, p-toluenesulfonic acid and monohydrate, and benzene are refluxed together using a Dean-Stark trap to azeotropically remove the evolved water. After cooling to room temperature and then adding dry ethyl ether, n-stearyl N$^e$-benzyloxycarbonyl-L-lysinate p-toluenesulfonate salt is collected by filtration, treated with 2M aqueous potassium bicarbonate solution, and extracted into dichloromethane. Evaporation gives the free amine, which is redissolved in dry tetrahydrofuran (THF) and added to a stirring solution of N$^a$-t-butyloxycarbonyl-N$^{im}$-benzyloxy-carbonyl-L-histidine, N-methylmorpholine, and isobutyl chloroformate in dry THF at −15° C. The resulting fully protected dipeptide ester is treated with 1/1 trifluoroacetic acid/dichloromethane at room temperature, neutralized with saturated aqueous sodium bicarbonate solution, and extracted into ethyl acetate. Evaporation gives the partially deblocked dipeptide, which is redissolved in dry THF and added to a stirring solution of benzyloxycarbonylglycine, N-methylmorpholine and isobutyl chloroformate in dry THF at −15° C. The formed, fully protected tripeptide ester is totally deblocked by treatment with hydrogen gas in glacial acetic acid at room temperature in the presence of Pd-C catalyst. Filtration, evaporation and purification on a microcrystalline cellulose column followed by lyophilization give the desired tripeptide ester as its triacetate salt.

The resultant molecule, glycyl-L-histidyl-L-lysine n-stearyl ester, was converted to the copper-complex by the addition of an equimolar quantity of copper diacetate. The pH was raised to neutrality with sodium hydroxide to obtain a produce useful for animal studies.

By substituting n-palmityl alcohol for the n-stearyl alcohol, glycyl-L-histidyl-L-lysine n-palmityl ester may be similarly synthesized.

EXAMPLE 4

A. Solid Phase Synthesis of glycyl-L-histidyl-L-lysyl-L-prolyl-L-valyl-L-phenylalanyl-L-valine::copper (II) and of glycyl-L-histidyl-L-lysyl-L-valyl-L-phenylalanyl-L-valine:copper (II)

These peptides are synthesized by standard cold-phase methods common to the peptide field (J. Stewart and J. Young, *Solid Phase Peptide Synthesis*, Pierce Chemical Co., 1984). Briefly stated, Boc-Val-O-Resin was sequentially coupled with other blocked amino acids using dicyclohexylcarbodiimide as a reaction agent. Protected amino acids, resins for solid-phase synthesis, and coupling agents were obtained from Peninsula Laboratories, San Carlos, Calif. Blocked amino acids are added in sequential order to obtain the desired peptide. The final peptide is deblocked using hydrogen fluoride. The final peptide is dissolved in 0.5% acetic acid and purified by passage through a Sephadex G-15 column (Pharmacia). Addition of equimolar cupric acetate, followed by lyophilization, produces the active molecule.

B. Solution Synthesis of glycyl-L-histidyl-L-lysyl-L-valyl-L-phenylalanyl-L-valine Multi-gram quantity of glycyl-L-histidyl-L-lysyl-L-valyl-L-phenylalanyl-L-valine was synthesized by standard solution phase method using t-butyloxycarbonyl protecting group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylmorpholine as coupling agent (2 hours at −20° C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, N$^a$-t-butyloxycarbonyl-N$^e$-benzyloxycarbonyl-L-lysine, N$^a$-t-butyloxycarbonyl-N$^{im}$-benzyloxycarbonyl-L-histidine, benzyloxycarbonylglycine) were added in sequential order to obtain the desired peptide. The final peptide was lyophilized from water and purified by liquid chromatography on a C-18 reverse-phase column to produce the desired hexapeptide in multi-gram quantity.

EXAMPLE 5

Synthesis of L-lysyl-L-histidyl-glycine

N$^a$-t-butyloxycarbonyl-N$^{im}$-benzyloxycarbonyl-L-histidine was dissolved in tetrahydrofuran (THF) and neutralized with one equivalent of N-methylmorpholine. It was then coupled with benzyl glycinate p-toluenesulfonate salt using isobutyl chloroformate and N-methylmorpholine. After two hours at −20° C. and an additional hour at ambient temperature, the reaction was quenched with 2N aqueous potassium bicarbonate. The product was extracted into ethyl acetate, washed first with 1M aqueous citric acid, and second with saturated sodium bicarbonate. The organic phase was dried over anhydrous sodium sulfate. Filtration and evaporation gave benzyl $N^\alpha$-t-butyloxycarbonyl-$N^{im}$-benzyloxycarbonyl-L-histidyl-glycinate.

This product was dissolved in anhydrous methanolic hydrogen chloride (saturated at 0° C.) for 5 minutes, followed by removal of solvent under reduced pressure, forming benzyl $N^{im}$-benzyloxycarbonyl-L-histidyl-glycinate. This was dissolved in tetrahydrofuran, and isobutyl chloroformate, N-methylmorpholine and $N^\alpha,N^\epsilon$-dibenzyloxycarbonyl-L-lysine were added to form benzyl $N^\alpha,N^\epsilon$-dibenzyloxycarbonyl-L-lysyl-L-histidyl-glycinate (3 hours at $-20°$ C., then 1 hour at ambient temperature). This product was then dissolved in methanol/acetic acid [1:1 (v/v)] and hydrogenated overnight in the presence of 10% Pd-C catalyst. The resultant L-lysyl-L-histidyl-glycine was lyophilized from water several times, then purified by liquid chromatography on a C-18 reverse phase column to yield the desired tripeptide triacetate salt as a foamy white solid.

EXAMPLE 6

Synthesis of L-lysyl-L-histidyl-glycyl-L-valyl-L-phenylalanyl-L-valine

Multi-gram quantity of L-lysyl-L-histidyl-glycyl-L-valyl-L-phenylalanyl-L-valine was synthesized by standard solution phase method using t-butyloxycarbonyl protecting group for the alpha nitrogen, benzyloxycarbonyl group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylmorpholine as coupling agents (2 hours at $-20°$ C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, t-butyloxycarbonylglycine, $N^\alpha$-t-butyloxycarbonyl-$N^{im}$-benzyloxycarbonyl-L-histidine, $N^\alpha,N^\epsilon$-dibenzyloxycarbonyl-L-lysine) were added in sequential order to obtain the desired peptide. The final peptide was completely deprotected using hydrogen gas in glacial acetic acid for 5 days in the presence of 10% Pd-C catalyst. The final peptide was lyophilized from water and purified by liquid chromatography on a C-18 reverse-phase column to produce the desired hexapeptide in multi-gram quantity.

The above systematic synthesis proved advantageous over some of the solid-phase methods in providing multi-gram quantity of the desired peptide in high purity with minimal purification.

EXAMPLE 7

Shay Model Studies

Stomach ulcers were induced in rates by the Shay procedure. Briefly stated, the passage between the stomach and the intestine in the rat is tied off, thereby causing a buildup of stomach acid, resulting in ulceration. For treatment, the rats received 10 mg of GHL or GHL-Cu or a derivative thereof in 0.25 ml saline intubated into the stomach. Control rats received saline only. After 24 hours, the stomachs were photographed and the stomach acidity determined.

The results of the experiments are shown in Table 1, which depicts the inhibition of stomach acid accumulation and stimulation of cytoprotective mucous secretion in the rats. The mucous production was visually rated from 0 to $++++$, where 0 represented substantially no mucous observed and $++++$ represented a very heavy mucous secretion.

TABLE 1

|  | Stomach acidity pH ± standard deviation | Mucous Production |
|---|---|---|
| Control | 2.01 ± 0.27 | Unobservable |
| GHL | 3.26 ± 0.47 | ++ |
| GHL + GHL-Cu | 6.52 ± 0.70 | ++++ |
| GHL-Cu | 6.94 ± 0.25 | ++++ |

EXAMPLE 8

Shay Model Studies

Stomach ulcers were induced in rats by the Shay procedure. Briefly, the passage between the stomach and the intestine in the rat is tied off, thereby causing a buildup of stomach acid. Ulcer formation is visible after 18–24 hours of ligation.

For treatment, the rats received either GHL-Cu or a derivative in 0.25 ml of saline into the stomach via a gastric feeding tube immediately after the surgical procedure. Control rats received saline only. After 24 hours, the rats were sacrificed, the stomachs were removed and photographed. The acidity of the stomach contents was also measured.

In the experiments reported here, the rats were treated with various doses of glycyl-L-histidyl-L-lysine (GHL), GHL-Cu (2:1), or GHL-Cu (1:1) complex of various analogs of GHL as the 1:1 copper complexes.

Stomach ulcers were induced in groups of rats as described above. The animals were dosed with increasing amounts of either GHL:Cu at a molar ration of 2 moles of GHL to 1 mole of Cu (2:1), equimolar complex (1:1), and GHL without copper. After 24 hours, the stomachs were removed, the pH was determined and the percent of stomachs with visible ulcers was determined.

The results of a series of experiments are presented in Table 2, which shows the inhibition of stomach acid secretion (as shown by the higher pH of the stomach fluid when compared with the control), and the percentage of the stomachs which demonstrated visible ulcers. The presence of ulcers is scored positive if a single lesion is noted, regardless of the size. The saline treated stomachs had multiple large lesions, while treated animals had smaller, less numerous ulcers if present. Both the glycyl-L-histidyl-L-lysine:Cu (2:1) and glycyl-L-histidyl-L-lysine:Cu (1:1) inhibited ulcer formation and raised the pH of the stomach contents in a dose responsive manner.

TABLE 2

| INHIBITION OF STOMACH ULCER FORMATION AND ACID SECRETION BY GHL COPPER COMPLEXES | | | | |
|---|---|---|---|---|
| COMPOUND | DOSE | N | pH | % WITH ULCERS |
| SALINE | — | 25 | 2.06 ± 0.61 | 72% |
| GHL | 10 mg | 5 | 2.84 ± 0.90 | 40% |
| GHL-Cu(2:1) | 3 mg | 2 | 2.72 ± 1.03 | 50% |
| GHL-Cu(2:1) | 10 mg | 2 | 6.38 ± 1.01 | 11% |

TABLE 2-continued

INHIBITION OF STOMACH ULCER FORMATION AND ACID SECRETION BY GHL COPPER COMPLEXES

| COMPOUND | DOSE | N | pH | % WITH ULCERS |
|---|---|---|---|---|
| GHL-Cu(1:1) | 1 mg | 7 | 3.80 ± 1.34 | 33% |
| GHL-Cu(1:1) | 3 mg | 8 | 4.85 ± 1.17 | 0% |
| GHL-Cu(1:1) | 10 mg | 13 | 7.23 ± 0.64 | 0% |

Figure 1:
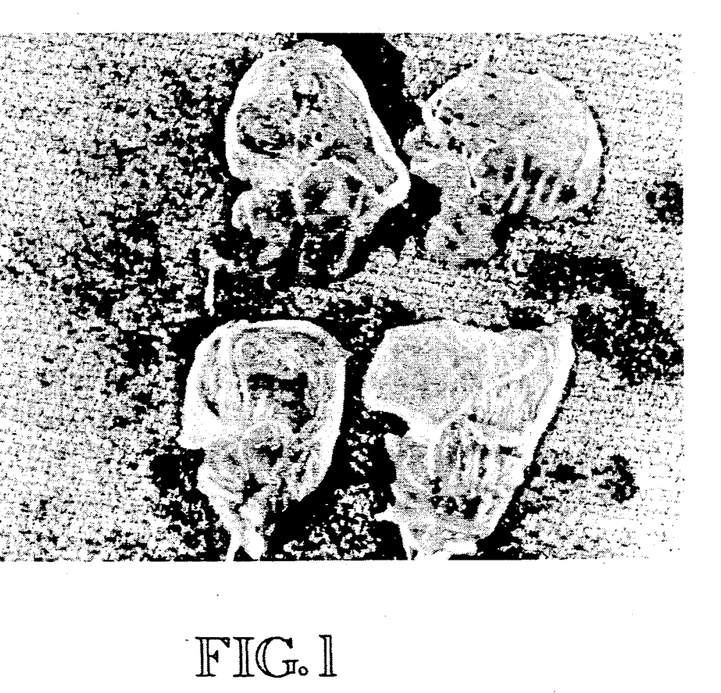
FIG. 1 is a photograph of rat stomachs, illustrating the ulcerations in control animals as compared to treated animals. The circled black dots in the stomach wall are stomach ulcers.
Figure 2:
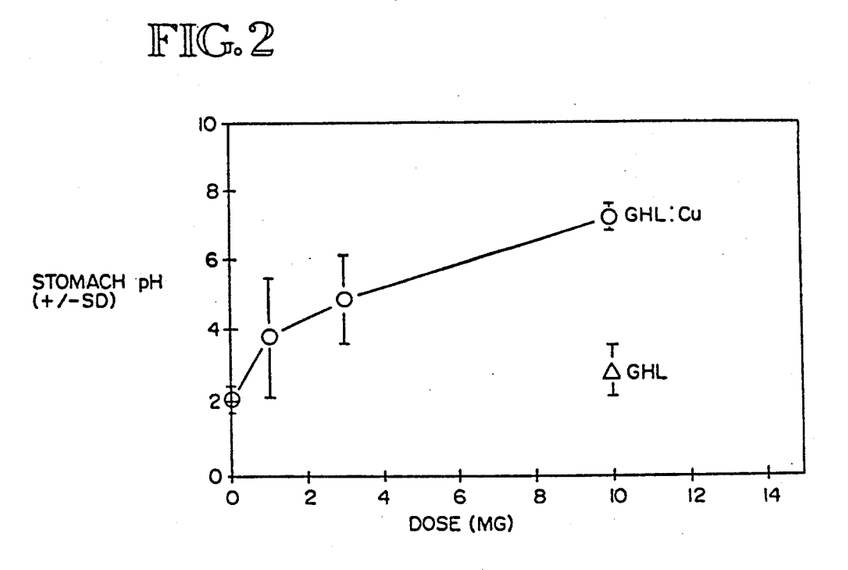
FIG. 2 depicts the increase in stomach pH (indicating a stomach acid secretion) with an increasing dosage of GHL-Cu.
Figure 3:
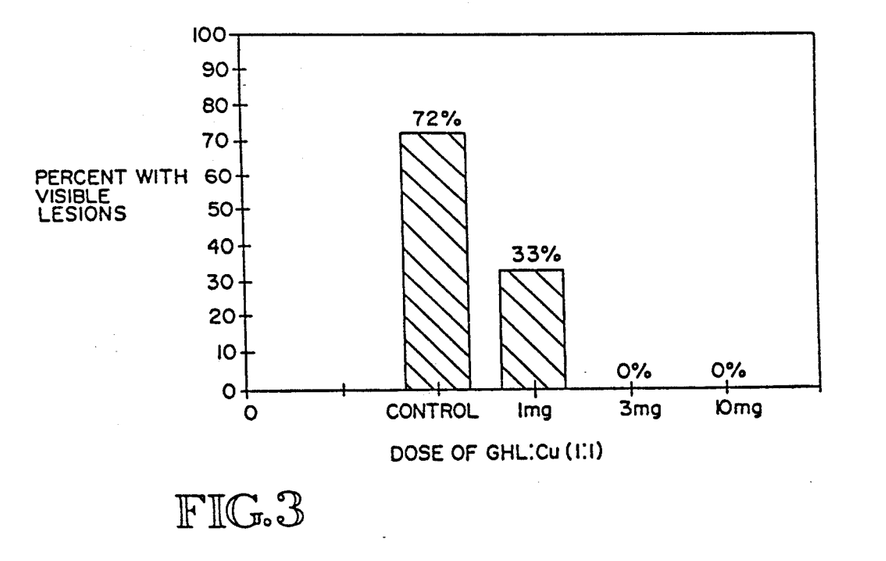
FIG. 3 illustrates the decrease in visible ulcer formation with an increasing dosage of GHL-Cu.

Representative photographs of rat stomachs from a typical experiment are reproduced in FIG. 1. The top photographs illustrate salinetreated stomachs after 24 hours and show multiple ulcer lesions. The bottom photographs illustrate treatment with GHL-Cu (1:1), 10 mg, and show complete inhibition of lesion formation. The increasing stomach pH (indicating a decrease in stomach acid secretion) with increasing dose of GHL-Cu (1:1) is also shown in FIG. 2. The decrease in visible ulcer formation with the corresponding dosages of GHL-Cu is shown in FIG. 3.

Analogs of glycyl-L-histidyl-L-lysine also have been found to inhibit ulcer formation in the rat model. A summary of some of the analogs tested is shown in Table 3. All of the compounds have been tested as the 1:1 copper complex.

TABLE 3

INHIBITION OF STOMACH ULCER FORMATION AND ACID SECRETION BY GHL AND LHG ANALOG COPPER COMPLEXES

| COMPOUND | DOSE | N | pH | % WITH ULCERS |
|---|---|---|---|---|
| SALINE | — | 25 | 2.06 ± 0.61 | 72% |
| GHL octyl ester:Cu | 3 mg | 8 | 3.50 ± 1.18 | 25% |
| GHL octyl ester:Cu | 10 mg | 8 | 6.18 ± 0.98 | 0% |
| LGH-Cu | 3 mg | 9 | 3.61 ± 1.00 | 11% |
| GH(1-methyl)L:Cu | 1 mg | 6 | 2.17 ± 0.82 | 17% |
| GHL pentadecyl ester:Cu | 3 mg | 6 | 3.27 ± 0.82 | 0% |

EXAMPLE 9

Healing of Duodenal Ulcers

Cysteamine will induce chronic duodenal ulcers in rats when injected subcutaneously (Olsen, P. S., Poulsen, S. S., Therkelsen, K., and Nexo, E., Oral administration of synthetic human urogastrone promotes healing of chronic duodenal ulcers in rats, *Gastroenterology* 90:911-917 (1986)).

Duodenal ulcers were induced in a group of 40 S.D. rats (male and female) by subcutaneous injections of cysteamine (350 mg/kg and 175 mg/kg) 6 hours apart. Saline was injected subcutaneously (5 cc) to provide fluid. Surviving animals (n=34) were followed for 7 days then laparotomies were performed. External examinations of the duodenum were made to determine extent of adhesion of the liver or other surrounding tissues. Animals with duodenal ulcers were randomized (by sex) to receive GHL-Cu (2:1) in distilled water, or plain distilled water. Animals were maintained for 25 days after which they were sedated, stomachs and duodenums removed and dissected for internal inspection. The results were obtained and recorded, specimens immersed in 10% buffered formalin for analysis with a stereomicroscope.

The following rating scale was used to express severity of ulceration:

0—no indication of ulceration

1—mild ulceration, no extension through duodenum

2—moderate ulceration, fixation of surrounding tissue

3—extreme ulceration through duodenum

On the day of laparotomy, 28 rats (6 female, 12 male) were determined to have significant adhesion of the duodenum to surrounding tissues. These animals were randomized by sex to either the GHL-Cu or control group. Following 25 days of drinking water treatment (total dose per day of 0.6 mg/kg), rats were sedated and prepped for dissection. The stomach and duodenum were removed, notations made as to extent of residual adhesions. Internal inspection of the duodenum was made prior to immersion of specimen in 10% formalin. Results at the time of gross inspection indicated 11 out of 14 control animals had significant residual ulcerations extending to the liver primarily. GHL-Cu animals demonstrated somewhat milder ulcerations in 7 out of 14 animals.

The results from microscopic examination and rating of ulcer severity were as follows:

| Rating | # Control Animals | # GHL-Cu(2:1)Animals |
|---|---|---|
| 0 | 1 | 4 |
| 1 | 2 | 5 |
| 2 | 6 | 3 |
| 3 | 5 | 2 |

Figure 4:
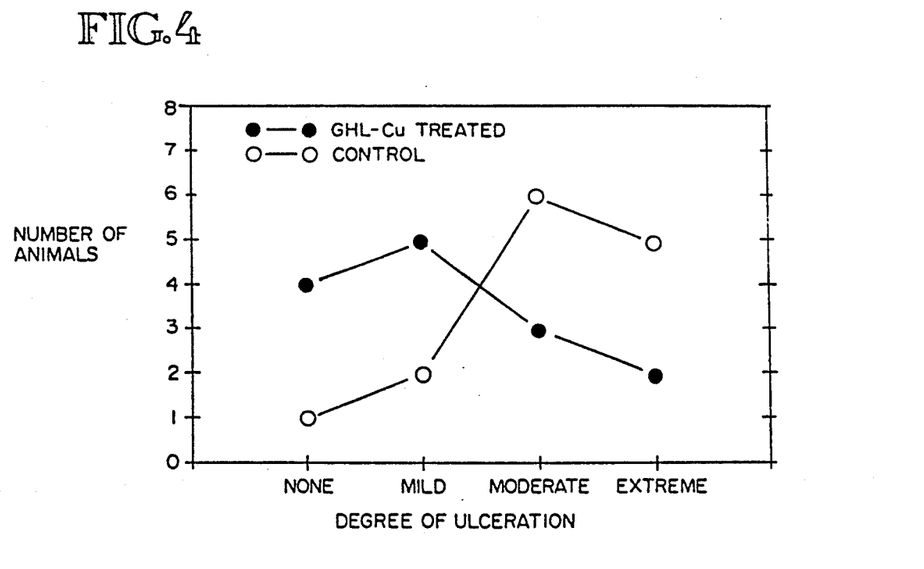
FIG. 4 depicts the healing of duodenal ulceration observed following drinking water treatment.

The degree of ulceration is displayed graphically in FIG. 4.

In summary, indications are that GHL-Cu (2:1) animals benefited from treatment when compared to controls. Although ulcers were present in most GHL-Cu rats, the severity was reduced. Four animals had no demonstrable ulcers at the time of microscopic inspection. The depth of ulcer penetration was reduced in the GHL-Cu group.

EXAMPLE 10

Ethanol-Induced Gastric Ulcers

A series of ethanol induced gastric ulcer studies was conducted. Ulcers were induced by oral administration of 95% ethyl alcohol (*Scan. J. Gastroenterol* 23:665-671 (1988)). The studies were conducted to determine both the preventative and healing effects of glycl-L-histidyl-L-lysine:Cu.

Dose Response of Ethanol

An initial dose response study was performed to determine the optimal dose of ethanol for ulcer formation. Following a 12 hour fast, groups of 300-400 gm SD rats were infused with increasing amounts of ethanol via a gastric feeding tube. The following doses were used:

1.25 ml/kg (n=3)

2.5 ml/kg (n=3)

5.0 ml/kg (n=3)

After one hour, the rats were overdosed with pentobarbital and the stomachs were removed. Inspection of the gastric mucosa revealed multiple large superficial ulcers including blood vessel erosion. Severe "pitting" type ulcers could be seen in all the dose groups. The 5.0 mg/kg group experienced the most severe damage to the gastric mucosa, the 1.25 mg/kg group the least damage.

Ulcer Prevention

A dose of 2.0 ml/kg 95% ethanol was chosen to induce gastric ulcers in rats. Prior to the ethanol ingestion, three groups of rats were pretreated with 0.5 ml of 2% glycyl-L-histidyl-L-lysine:Cu (1:1) as follows:

Group 1: 2 hours prior to Ethanol dosing
Group 2: 4 hours prior to Ethanol dosing
Group 3: 6 hours prior to Ethanol dosing In addition, 4 rats served as controls with no pretreatment. One hour following ethanol administration, the stomachs were removed and inspected for ulceration as described above. All controls had ulcers similar to those seen in the dose response study, that is, red superficial ulcerations involving blood vessels in the stomach wall.

The pretreatment with glycyl-L-histidyl-L-lysine:Cu (1:1) gave the following results:

Group 1: 2 hours prior—No evidence of ulceration
Group 2: 4 hours prior—Significantly better than controls, however, small ulcers were visible.
Group 3: 6 hours prior—Mixed results. One rat had multiple lesions much like the control group. One rat had no visible ulcers, one rat had small ulcers similar to the 4 hour group.

Figure 5:
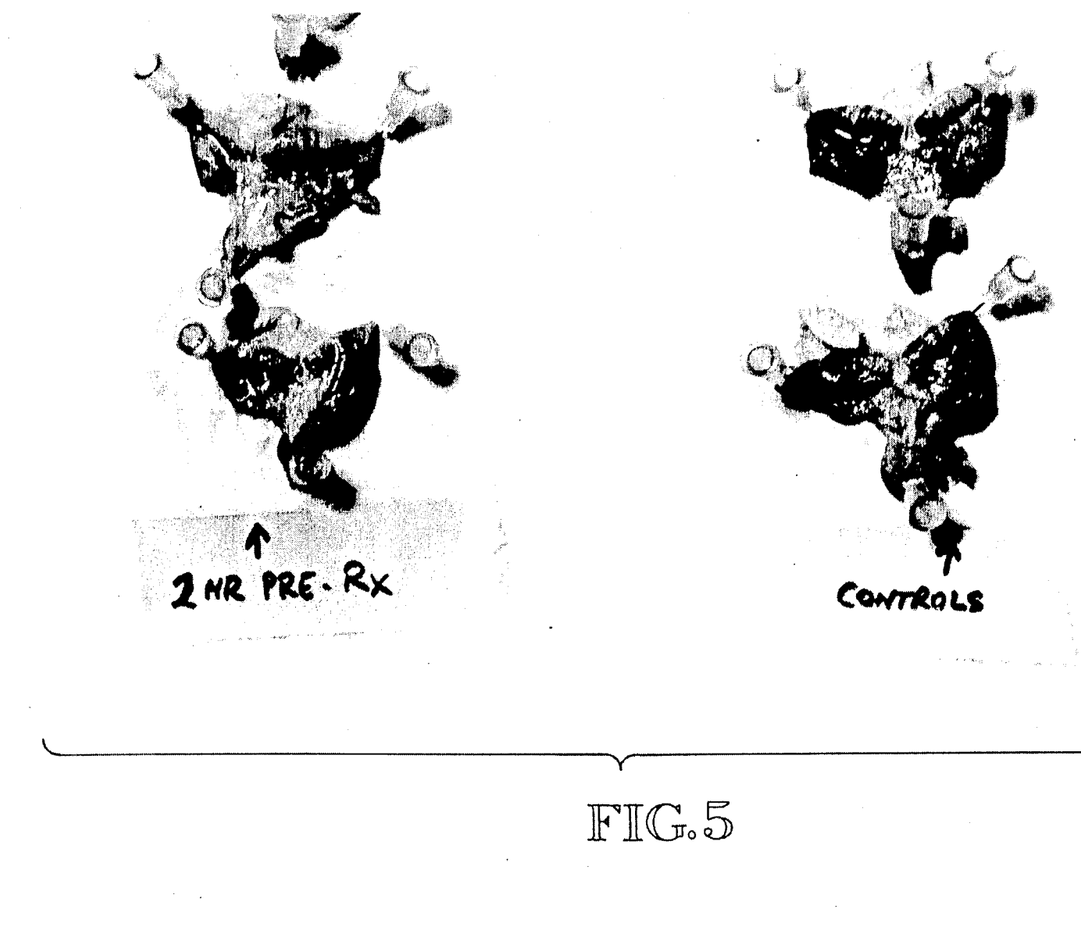
FIG. 5 is a photograph of rat stomachs, illustrating the inhibition of stomach ulcer formation by pretreatment with GHL-Cu.

Photographs of the control stomachs, i.e., no pretreatment (top photograph) and stomachs pretreated with GHL-Cu 2 hours prior to ethanol administration (bottom photograph) are shown in FIG. 5.

The pretreatment with the glycyl-L-histidyl-L-lysine:Cu (1:1) successfully inhibited gastric ulcer formation, totally blocking damage when administered 2 hours prior to 95% ethanol dosing.

Such results indicate that treatment of alcoholics, for example, with compounds of the present invention may prevent alcohol-induced gastric or duodenal ulcers commonly found in such subjects. Furthermore, pretreatment may reduce the amount of alcohol absorbed into the bloodstream, thus reducing the occurrence of a variety of undesired alcohol-related side effects.

Gastric Ulcer Healing

The ability of glycyl-L-histidyl-L-lysine:Cu (2:1) to heal ulcers induced by 95% ethanol has also been examined. In this study, ulcers were induced by administration of 4 ml/kg of 95% ethanol. The rats were then treated with glycyl-L-histidyl-L-lysine:Cu (2:1) in the drinking water at a dose of 0.01 mg/ml and 0.1 mg/ml (total dose per day of 1.6 mg/kg and 16 mg/kg, respectively). The rats were terminated at day 7 after ulcer induction and the stomachs examined for the presence of ulcers.

The following rating scale was used to express severity of ulceration:

0—no indication of ulceration
1—some irritation
2—small ulcers present
3—large ulcers present The results from the examination and rating of the ulcer severity were as follows:

| Rating | # Control Animals | # GHL-Cu Animals 0.01 mg/ml | 0.1 mg/ml |
|---|---|---|---|
| 0 | 2 | 5 | 5 |
| 1 | 0 | 2 | 1 |
| 2 | 3 | 0 | 1 |
| 3 | 2 | 0 | 0 |

Figure 6:
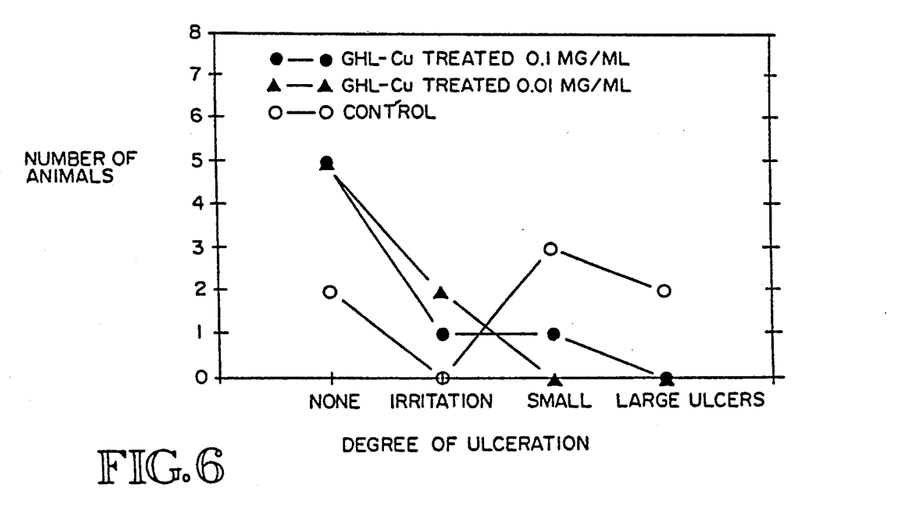
FIG. 6 illustrates the healing of ethanol-induced gastric ulcers.

The degree of ulceration is displayed graphically in FIG. 6.

The GHL-Cu treated animals at both dose levels benefited from the treatment when compared to controls. There were ulcers fewer ulcers present in the GHL-Cu treated rats and the severity of the existing ulcers was reduced. The majority of the animals had no demonstrable ulcers at the time of inspection.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for reducing the secretion of stomach acid in warm-blooded animals, comprising:
   administering to the animal a therapeutically effective amount of a composition comprising L-lysyl-L-histidyl-glycine.

2. A method for reducing the secretion of stomach acid in warm-blooded animals, comprising:
   administering to the animal a therapeutically effective amount of a composition comprising L-lysyl-L-histidyl-glycine:copper(II).

3. A method for reducing the secretion of stomach acid in warm-blooded animals, comprising:
   administering to the animal a therapeutically effective amount of a derivative of LHG-Cu having the general formula:

$$[\text{L-lysyl-L-histidyl-glycine-C(=O)—R}]:\text{copper(II)}$$

wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

4. A method for reducing the secretion of stomach acid in warm-blooded animals, comprising:
   administering to the animal a therapeutically effective amount of a derivative of LHG-Cu having the general formula:

$$[\text{X—L-histidyl-glycine-C(=O)—R}]:\text{copper(II)}$$

wherein X is glycyl-L-alanyl, glycyl-L-seryl, or glycyl-L-valyl, and wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

5. A method for reducing the secretion of stomach acid in warm-blooded animals, comprising:
   administering to the animal a therapeutically effective amount of glycyl-L-histidyl(1-methyl)-L-lysine:- copper(II) or L-lysyl-L-histidyl(1-methyl)glycine:-copper(II).

6. A method for increasing the secretion of cytoprotective mucous in the stomach of warm-blooded animals, comprising:
administering to the animal a therapeutically effective amount of a composition comprising L-lysyl-L-histidyl-glycine.

7. A method for increasing the secretion of cytoprotective mucous in the stomach of warm-blooded animals, comprising:
administering to the animal a therapeutically effective amount of a composition comprising L-lysyl-L-histidyl-glycine:copper(II).

8. A method for increasing the secretion of cytoprotective mucous in the stomach of warm-blooded animals, comprising:
administering to the animal a therapeutically effective amount of a derivative of LHG-Cu having the general formula:

wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

9. A method for increasing the secretion of cytoprotective mucous in the stomach of warm-blooded animals, comprising:
administering to the animal a therapeutically effective amount of a derivative of LHG-Cu having the general formula:

wherein X is glycyl-L-alanyl, glycyl-L-seryl, glycyl-L-valyl, and wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

10. A method for increasing the secretion of cytoprotective mucous in the stomach of warm-blooded animals, comprising:
administering to the animal a therapeutically effective amount of glycyl-L-histidyl(1-methyl)-L-lysine:-copper(II) or L-lysyl-L-histidyl(1-methyl)-glycine:copper(II).

11. A method for reducing the formation of stomach ulcers in warm-blooded animals, comprising:
administering to the animal a therapeutically effective amount of a composition comprising L-lysyl-L-histidyl-glycine.

12. A method for reducing the formation of stomach ulcers in warm-blooded animals, comprising:
administering to the animal a therapeutically effective amount of a composition comprising L-lysyl-L-histidyl-glycine:copper(II).

13. A method for reducing the formation of stomach ulcers in warm-blooded animals, comprising:
administering to the animal a therapeutically effective amount of a derivative of LHG-Cu having the general formula:

wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

14. A method for reducing the formation of stomach ulcers in warm-blooded animals, comprising:
administering to the animal a therapeutically effective amount of a derivative of LHG-Cu having the general formula:

wherein X is glycyl-L-alanyl, glycyl-L-seryl, or glycyl-L-valyl, and wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

15. A method for reducing the formation of stomach ulcers in warm-blooded animals, comprising:
administering to the animal a therapeutically effective amount of glycyl-L-histidyl(1-methyl)-L-lysine:-copper(II) or L-lysyl-L-histidyl(1-methyl)-glycine:copper(II).

16. A method for healing stomach or intestinal ulcers in warm-blooded animals, comprising:
administering to animal a therapeutically effective amount of a composition comprising glycyl-L-histidyl-L-lysine.

17. A method for healing stomach or intestinal ulcers in warm-blooded animals, comprising:
administering to the animal a therapeutically effective amount of a composition comprising glycyl-L-histidyl-L-lysine:copper(II).

18. A method for healing stomach or intestinal ulcers in warm-blooded animals, comprising:
administering to the animal a therapeutically effective amount of a derivative of GHL-Cu having the general formula:

wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

19. A method for healing stomach or intestinal ulcers in warm-blooded animals, comprising:
   administering to the animal a therapeutically effective amount of a derivative of GHL-Cu having the general formula:

wherein X is glycyl-L-alanyl, glycyl-L-seryl, or glycyl-L-valyl, and wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

20. A method for healing stomach or intestinal ulcers in warm-blooded animals, comprising:
   administering to the animal a therapeutically effective amount of glycyl-L-histidyl(1-methyl)-L-lysine:copper(II).

21. A method for healing stomach or intestinal ulcers in warm-blooded animals, comprising:
   administering to the animal a therapeutically effective amount of a composition comprising L-lysyl-L-histidyl-glycine.

22. A method for healing stomach or intestinal ulcers in warm-blooded animals, comprising:
   administering to the animal a therapeutically effective amount of a composition comprising L-lysyl-L-histidyl-glycine:copper(II).

23. A method for healing stomach or intestinal ulcers in warm-blooded animals, comprising:
   administering to the animal a therapeutically effective amount of a derivative of LHG-Cu having the general formula:

wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

24. A method for healing stomach or intestinal ulcers in warm-blooded animals, comprising:
   administering to the animal a therapeutically effective amount of a derivative of LHG-Cu having the general formula:

wherein X is glycyl-L-alanyl, glycyl-L-seryl, or glycyl-L-valyl, and wherein R is selected from the group consisting of alkyl moieties containing from 1 to 18 carbon atoms, aryl moieties containing from 6 to 12 carbon atoms, alkoxy moieties containing from 1 to 18 carbon atoms, and aryloxy moieties containing from 6 to 12 carbon atoms, or where R is L-prolyl-L-valyl-L-phenylalanyl-L-valine or L-valyl-L-phenylalanyl-L-valine.

25. A method for healing stomach or intestinal ulcers in warm-blooded animals, comprising:
   administering to the animal a therapeutically effective amount of glycyl-L-histidyl(1-methyl)-L-lysine:copper(II) or L-lysyl-L-histidyl(1-methyl)-glycine:copper(II).

* * * * *

UNITED STATES PATENT AND TRADEMARK OFFICE
CERTIFICATE OF CORRECTION

PATENT NO. : 5,023,237
DATED : June 11, 1991
INVENTOR(S) : Loren R. Pickart

It is certified that error appears in the above-identified patent and that said Letters Patent is hereby corrected as shown below:

In column 16, claim 18, line 64 please delete:

$$\text{"[glycyl-L-histidyl-lysine-}\overset{\overset{O}{\|}}{C}\text{-R]:copper(II)"}$$

and substitute therefor, $$\text{-- [glycyl-L-histidyl-L-lysine-}\overset{\overset{O}{\|}}{C}\text{-R]:copper(II) --.}$$

Signed and Sealed this

Twenty-seventh Day of October, 1992

Attest:

DOUGLAS B. COMER

*Attesting Officer*   *Acting Commissioner of Patents and Trademarks*

UNITED STATES PATENT AND TRADEMARK OFFICE
CERTIFICATE OF CORRECTION

PATENT NO. : 5,023,237

DATED : June 11, 1991

INVENTOR(S) : Loren R. Pickart

It is certified that error appears in the above-identified patent and that said Letters Patent is hereby corrected as shown below:

In column 16, claim 18, line 64 please delete:

"[glycyl-L-histidyl-lysine-$\overset{\overset{\text{O}}{\|}}{\text{C}}$-R]:copper(II)"

and substitute therefor:

-- [glycyl-L-histidyl-L-lysine-$\overset{\overset{\text{O}}{\|}}{\text{C}}$-R]:copper(II) --.

Signed and Sealed this

Twenty-fourth Day of November, 1992

Attest:

DOUGLAS B. COMER

Attesting Officer

Acting Commissioner of Patents and Trademarks